(12) United States Patent
Lilien et al.

(10) Patent No.: US 10,197,610 B2
(45) Date of Patent: Feb. 5, 2019

(54) METHOD AND SYSTEM FOR DETERMINING THE THERMAL POWER LINE RATING

(71) Applicants: Université de Liège, Interface Entreprises-Université, Angleur (BE); Ampacimon S.A., Angleur (BE)

(72) Inventors: Jean-Louis Lilien, Angleur (BE); Huu-Minh Nguyen, Liège (BE); Bertrand Godard, Liège (BE)

(73) Assignee: Ampacimon S.A., Grâce-Hollogne (BE)

( * ) Notice: Subject to any disclaimer, the term of this patent is extended or adjusted under 35 U.S.C. 154(b) by 604 days.

(21) Appl. No.: 14/579,792

(22) Filed: Dec. 22, 2014

(65) Prior Publication Data

US 2016/0178681 A1    Jun. 23, 2016

(51) Int. Cl.
*G01R 31/02* (2006.01)
*G01R 19/00* (2006.01)
(Continued)

(52) U.S. Cl.
CPC ............. *G01R 31/021* (2013.01); *G01C 5/00* (2013.01); *G01N 25/00* (2013.01);
(Continued)

(58) Field of Classification Search
CPC .................................................. G01R 31/021
(Continued)

(56) References Cited

U.S. PATENT DOCUMENTS 5,933,355 A * 8/1999 Deb ........................ H02J 3/00
                                                      702/3
6,205,867 B1   3/2001 Hayes et al.
(Continued)

FOREIGN PATENT DOCUMENTS

WO    WO 2010/054072 A1    5/2010
WO    WO 2014/090416 A1    6/2014

OTHER PUBLICATIONS

Tapani Seppa et al./CIGRE; Guide for Selection of Weather Parameters for Bare Overhead Conductor Ratings; Brochure No. 299; Aug. 2006; 55 pages.
(Continued)

*Primary Examiner* — Ricky Ngon
(74) *Attorney, Agent, or Firm* — Reinhart Boerner Van Deuren P.C.

(57) ABSTRACT

Method for measuring the power line thermal rating or maximum allowable current rating of an overhead power line with respect to a suspended/anchored cable span (2), comprising at least the following steps of:
  monitoring a motion of at least one point P of said suspended/anchored cable span (2) over a time interval;
  monitoring actual line current I, in A, over said time interval;
  determining an actual sag of said suspended/anchored cable, as a variable of actual line current;
  measuring or determining the effective wind speed of said suspended/anchored cable span (2) over said time interval;
  determining a sag reserve DF, in m, for thermal rating, which is the distance between the actual sag and a maximum allowable sag;
  determining the rate of change, $\tan(\alpha)$, in $m/A^2$, of the actual sag versus the square of the line current for the effective wind speed;
and
  determining the power line thermal rating of the overhead power line, or ampacity, linked to a corresponding safety clearance, at measured or determined effective wind speed, by adding the square of actual current I to the ratio of the sag reserve DF by the sag rate of change,
(Continued)

tan(α), at the effective wind speed, and taking the square root of that addition, i.e.

$$\text{Ampacity} = \sqrt{I^2 + \frac{DF}{\tan(\alpha)}},$$

wherein ampacity is in amperes.

8 Claims, 14 Drawing Sheets

(51) Int. Cl.
*G01N 25/00* (2006.01)
*H02G 7/02* (2006.01)
*H02J 3/00* (2006.01)
*G01C 5/00* (2006.01)

(52) U.S. Cl.
CPC ........... *G01R 19/0092* (2013.01); *H02G 7/02* (2013.01); *H02J 3/00* (2013.01); *H02J 2003/007* (2013.01); *Y02E 60/74* (2013.01); *Y04S 10/30* (2013.01)

(58) Field of Classification Search
USPC ........................................................ 702/64
See application file for complete search history.

(56) References Cited

U.S. PATENT DOCUMENTS

| | | | |
|---|---|---|---|
| 8,184,015 B2 | 5/2012 | Lilien et al. | |
| 8,744,790 B2* | 6/2014 | Lancaster | G01R 21/06 702/64 |
| 9,158,036 B2* | 10/2015 | Liu | G01W 1/02 |
| 2009/0138229 A1* | 5/2009 | Engelhardt | G01C 9/00 702/130 |
| 2009/0243876 A1* | 10/2009 | Lilien | H02G 1/02 340/870.01 |
| 2010/0114392 A1* | 5/2010 | Lancaster | G01R 21/06 700/292 |
| 2014/0180616 A1* | 6/2014 | Aaserude | G01R 27/02 702/65 |

OTHER PUBLICATIONS

R. Stephen et al./CIGRE; Thermal Behaviour of Overhead Conductors; Brochure No. 207; Aug. 2002; 46 pages.
D. Douglas et al./CIGRE; SAG-Tension Calculation Methods for Overhead Lines; Brochure No. 324; Jun. 2007; 90 pages.
R. Stephen et al./CIGRE; Guide for Application of Direct Real-Time Monitoring Systems; Brochure No. 498; Jun. 2012; 79 pages.
Anjan K. Deb; Powerline Ampacity System; published by CRC Press LLC in 2000; Boca Raton, FL; entire publication.
IEEE Power Engineering Society; IEEE Standard for Calculating the Current-Temperature of Bare Overhead Conductors; IEEE Std 738-2006; 2007; 69 pages.
F. Kiessling et al.; Overhead Power Lines; published by Springer-Verlag Berlin Heidelberg in 2003; New York; cover, first pages of book, and pp. 546-553.

* cited by examiner

METHOD AND SYSTEM FOR DETERMINING THE THERMAL POWER LINE RATING

TECHNICAL FIELD

The present invention is related to a method and system for determining the thermal power line rating (real-time and forecasted) with respect to an overhead electrical power line.

Maximum allowable current rating or ampacity is primarily limited by the need to maintain at least a minimum safety clearance around the sagging suspended/anchored span of electrically conductive cable to prevent arcing. Power line ratings could also be limited by maximum conductor temperature, due to material limitation(s), if reached before the maximum sag.

BACKGROUND

The maximum allowable constant electrical current rating having to meet the design, security and safety criteria, such as electrical clearance, of a particular power line on which an electrically conductive cable is used is known under the term "ampacity", as described for instance in "Sag-tension calculation methods for overhead lines", published in 2007 as CIGRE Technical Brochure No. 324 by Study Committee B2 of the International Council on Large Electric Systems (CIGRE).

Power line rating (i.e. ampacity) can be dynamically estimated using smart sensors. The so-called dynamic line rating is nowadays considered with great interest in everyday operation of power networks all around the world. Forecasted values of ampacity are also used in day-ahead network management as well in several days ahead network market approach, while even very long term approach may be used for planning. Medium- and long-term, i.e. over about four hours, forecasted values are based on forecasted meteorological data whereas real-time and short-time ampacity forecasts are based on real-time and possibly short past analysis of actual conditions acting on the power lines, like time series. Those conditions, including wind speed, wind direction, and ambient temperature for example may be locally measured, computed or inferred from actual observations on or near the field. Most generally, measurements, computations and actual observations may be combined by appropriate stochastic tools to deduce the forecasted power line rating values.

Methods to evaluate the ampacity of a suspended/anchored cable span on the basis of various data are explained for instance in A. Deb, "Power line ampacity system", published in 2000 by CRC Press, and in technical brochures from international organizations, such as CIGRE Technical Brochures No. 207 ("Thermal behavior of overhead conductors") and No. 498 ("Guide for application of direct real-time monitoring systems"), respectively published in 2002 and 2012, as well as in abovementioned CIGRE Technical Brochure No. 324. The methods disclosed in these documents use weather data as locally measured or simulated following international recommendations as explained, for example, in CIGRE Technical Brochure No. 299 ("Guide for the selection of weather parameters for bare overhead conductor ratings"), published in 2006 or IEEE Standard 738-2006—IEEE Standard for Calculating the Current-Temperature of bare Overhead Conductors, published in 2007.

The ampacity calculation is also based on the ruling span concept which allows to replace a full multi-span section by one equivalent so-called "ruling span" which is theoretically giving access to all individual span behaviors but many hypotheses lie behind that theory (Kiessling et al, "Overhead power lines", Springer 2003, page 548).

Thus, all existing models so far usually use the ruling span concept coupled with the state change equation (Kissling et al, ibid., page 546) and thermal equations including meteorological data, conductor data, sagging conditions, etc.

As explained in U.S. Pat. No. 8,184,015, continuous monitoring of electrical power lines, in particular high-voltage overhead lines, is essential to timely detect anomalous conditions which could lead to a power outage. Measurement of the sag of power line spans between successive supports to determine whether the sag is greater than a maximum value has become a mandatory requirement in some countries.

U.S. Pat. No. 8,184,015 discloses a device and method for continuously monitoring the sag on a power line span. This method allows the determination of mechanical dynamic properties of the power lines just by sensing mechanical vibrations in a frequency range from 0 to some tens of Hertz. Indeed, power lines in the field are always subject to movements and vibrations, which may be very small but detectable by their accelerations in both time and frequency domains.

A number of different methods to measure the sag of a suspended/anchored cable span are also known. An example of tentative sag measurement consists in the optical detection of a target clamped on the monitored conductor by a camera fixed to a pylon, as disclosed in U.S. Pat. No. 6,205,867. Other examples of such methods include measurement of the conductor temperature or tension or inclination of conductor in the span. A conductor replica is sometimes attached to the tower to catch an assimilated conductor temperature without Joule effect.

Besides the fact that these methods only allow a partial monitoring of the power line, such methods suffer from other drawbacks: optical techniques are sensitive to reductions of the visibility induced by meteorological conditions while the other measurement methods depend on uncertain models and/or data which may be unavailable and/or uncertain, e.g. wind speeds, topological data, actual conductor characteristics, etc.

U.S. Pat. No. 5,933,355 discloses a software to evaluate ampacity of a power line. It is based on a thermal model and the ruling span concept.

U.S. Pat. No. 6,205,867 discloses a power line sag monitor based on inclination measurement. It is based on a thermal model and the ruling span concept.

International Publication No. WO 2010/054072 is related to real-time power line rating. It alleges the existence of a sensor about wind speed direction and amplitude but does not disclose how these sensors are constituted. It is based on a thermal model and the ruling span concept.

U.S. Patent Appl. Publ. No. 2014/0180616 is related to power line rating and is using conductor temperature sensor to calibrate IEEE theoretical model, based on actual observations of clearance by LIDAR and conductor temperature spot measurements. It relates to these two values by a linear regression. It is based on IEEE model correction and thus needs all data related to IEEE model, including conductor data, meteorological data and sagging data.

AIMS OF THE INVENTION

The present invention aims at providing a method to evaluate the ampacity of power lines which is not based on a model like existing ones (based on the ruling span concept, state change equation and thermal equilibrium).

The object of the invention is focused on the way to compute power line rating based on some sensor output, the sag for example, and the knowledge of effective wind speed (defined hereinafter) and ambient temperature (real-time or forecast) without any need of details on conductor data nor on power line data, except very few ones, like conductor diameter. As an example, power line rating obtention in relation with maximum sag (and thus clearance limitations) will not need to measure nor to compute conductor temperature.

SUMMARY OF THE INVENTION

First, in this disclosure, the effective wind speed is defined as the wind speed value for the considered span which is representative, for conductor mean temperature along the span, of the mean perpendicular wind speed cooling effect along the entire suspended cable span.

Now, the object of the invention is to solely use the outputs from a sensor giving recurrent access of one key parameter, like the sag, of at least one span of a power line section, coupled with (quasi-)simultaneous information about the effective wind speed acting on the same span and the knowledge of the actual load current flowing into the line. These kinds of sensors allow to gather, during a few months—typically three—one key parameter, the sag for example, versus the current flow (in amperes) at a given effective wind speed with a relative short interval of time, typically around a few minutes. Those outputs appropriately treated as discussed in this disclosure, are enough to determine the ampacity of the line forever, without any need of other data. It may be added that a watchdog of the key parameters, mainly one in fact, the so-called $\tan(\alpha)$ as discussed in this disclosure, used to determine the ampacity may be installed in order to regularly, every 6 months for example or on request, check any deviation, which would be due to abnormal line data or sagging changes, from initial values.

Accordingly, in at least one illustrative embodiment, this method comprises the steps of monitoring directly or indirectly (i.e. means through other variable like a camera, a GPS position, ultrasonic measurement, etc.) a variable such as sag, tension, position, temperature, etc., of at least one point of said suspended/anchored cable span over a time interval.

The sag may be measured, for instance, using the method disclosed in above-mentioned U.S. Pat. No. 8,184,015, which is incorporated by reference in the present patent application.

The effective wind speed component may be measured for instance, using the method disclosed in above-mentioned International Publication WO 2014/090416, which is incorporated by reference in the present patent application. If the effective wind speed is not an output of the sensor, it has to be deduced by appropriate measurement or deduced from other data or inputs.

In at least one embodiment, if the sag is an output of the sensor, maximum allowable sag for said suspended/anchored cable span must be known or measured. The "sag reserve" is then the subtraction of the actual sag measured on site from that maximum allowed value.

If other variables are measured, such as tension, temperature, position, their maximum or minimum value must be known in connection with minimum allowable clearance on that span/section. Thus "tension reserve", "temperature reserve" (or maximum temperature) or "position reserve" could be defined or any other variable representing the same effect on clearance.

In the case maximum conductor temperature is the limit (for material degradation limits) before clearance limitation arises, the system used must be able to properly determine the conductor temperature margin available in order to convert such margin into ampacity, as detailed in this disclosure.

Accordingly, the rate of change of the sag (or the other measured variable) versus the square (or an exponent very close to 2) of the current flow is evaluated. Implicitly, such a rate of change integrates all material, mechanical and meteorological acting parameters. As material (conductor data) and mechanical (geometrical sensitivity of sag change into a section of single or multi-span) parameters are quasi-constant (in the order of a few minutes) for a given real-time sag (or other variable depending on the sensor used), only meteorological parameters are influencing the rate of change of the sag. It can be noticed that ambient temperature and solar radiation, while they impact the sag value itself, do not impact significantly the rate of change of the sag with respect to the square of the current.

The power line thermal rating, if limited by clearance problem, is then deduced by the sole knowledge of the "sag reserve", or other "variable reserve", like temperature reserve, tension reserve or position reserve, as well as the sag measurement, and its rate of change with respect to the square of the current, as explained in the detailed description of the invention.

The power line thermal rating limited by maximum conductor temperature (due to material degradation) before clearance limitations appear will need one further step, as explained later in the detailed description of the invention. This invention does not need any conductor temperature measurement but may use it if confidently available.

Accordingly, in at least one embodiment, a maximum allowable current rating for said suspended/anchored span of electrically conductive cable is determined according to the above-mentioned method for this purpose, and a current passing through said power line is limited at or below said maximum allowable current rating. If the power line comprises a plurality of successive suspended/anchored cable spans, a maximum allowable current rating may be calculated for each one of these suspended/anchored cable spans, or for a subset of these suspended/anchored cable spans which has previously been identified as critical[1], and the current passing through said power line may then be limited at or below the lowest of these maximum allowable current ratings.

[1] A critical span in a multi-span section is a span that may reach the maximum allowable sag on that span before other spans. That may be due to specific conditions like lower perpendicular wind speed due to screening effect or orientation, obstacles (like trees for example) that may grow more quickly compared to other situations along the line, etc. There are possibly several critical spans in one section, each of them being critical in different situations of external weather or local consideration.

The present invention also relates to computer programs and memory carriers containing computer-readable instruction sets for implementing these methods.

The above summary of some example embodiments is not intended to describe each disclosed embodiment or every implementation of the invention. In particular, selected features of any illustrative embodiment within this specification may be incorporated into an additional embodiment unless clearly stated to the contrary.

BRIEF DESCRIPTION OF THE DRAWINGS

The invention may be more completely understood in consideration of the following detailed description of embodiments in connection with the accompanying drawings, in which:

FIG. 12 is the sag vs conductor temperature with a curve slope below the knee-point equal to $\alpha_1$. It is obtained in a similar way as on FIG. 6;

FIG. 13 is the sag of the conductor span vs. the square of the current flow with a curve slope below the knee-point equal to $\alpha_2$ which is the same $\alpha_2$ as the one shown on FIG. 10;

FIG. 14 is the conductor temperature vs. the square of the current flow with a slope parameter $\lambda\beta$, with $\lambda\beta=\tan(\alpha_2)/\tan(\alpha_1)$;

Figure 1:
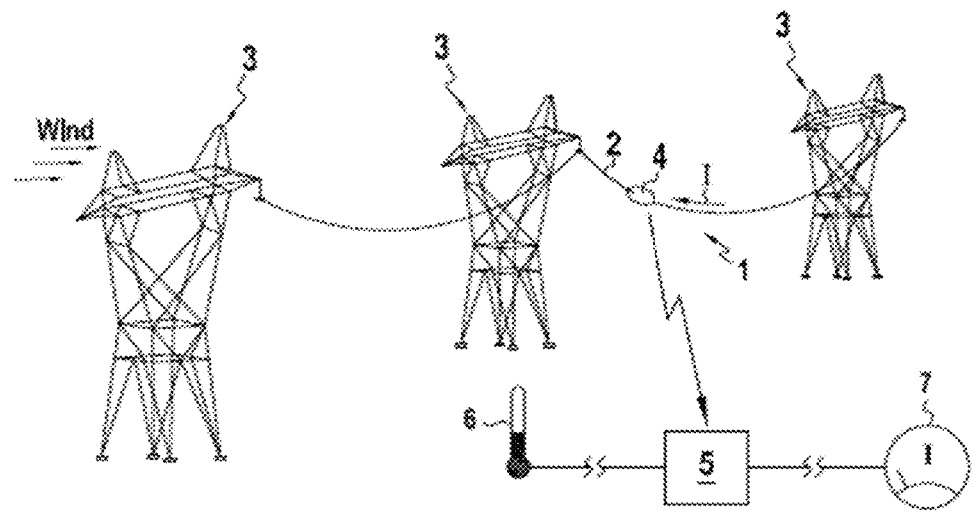
FIG. 1 is a schematic view of a power line with a plurality of spans of suspended/anchored electrically conductive cable and an example of a system for determining a maximum allowable current rating for this span.

Unless stated otherwise, all preceding figures and observation points are given for illustrative purpose only and are based on actual measurements or simulations on a 150 kV line, in a multi-span section, all aluminum alloy conductor AAAC 445: diameter=27.45 mm; m=1230 kg/km. Line parameters are the following: ruling span length=342.31 m, span length under supervision=369 m, emissivity=0.9, absorptivity=0.7.

While the invention is amenable to various modifications and alternative forms, specifics thereof have been shown by way of example in the drawings and will be described in detail hereinafter. It should be understood, however, that the intention is not to limit aspects of the invention to the particular embodiments described. On the contrary, the intention is to cover all modifications, equivalents, and alternatives falling within the scope of the invention.

DESCRIPTION OF DETAILED EMBODIMENTS OF THE INVENTION

As to the following defined terms, these definitions shall be applied, unless a different definition is given in the claims or elsewhere in this specification.

All numeric values are herein assumed to be preceded by the term "about", whether or not explicitly indicated. The term "about" generally refers to a range of numbers that one of skill in the art would consider equivalent to the recited value (i.e. having the same function or result). In many instances, the term "about" may be indicative as including numbers that are rounded to the nearest significant number.

Although some suitable dimension ranges and/or values pertaining to various components, features and/or specifications are disclosed, one of skill in the art, incited by the present disclosure, would understand that desired dimensions, ranges and/or values may deviate from those expressly disclosed.

As used in this specification and in the appended claims, the singular forms "a", "an", and "the" include plural referents unless the content clearly dictates otherwise. As used in this specification and in the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

The present invention relates to measuring a power line thermal rating with respect to a suspended/anchored cable span. This consists in providing a maximum allowable current rating, also known as "ampacity", for such a suspended/anchored cable span or for an electric power line comprising such a suspended/anchored cable span.

FIG. 1 schematically illustrates an overhead power line 1 comprising a plurality of successive suspended/anchored spans 2 of electrically conductive cable supported by pylons 3. On some suspended/anchored cable span 2 (the critical ones[2]) is clamped an autonomous device 4, as disclosed for instance in abovementioned U.S. Pat. No. 8,184,015, comprising an accelerometer set suitable for monitoring motion in at least two axes perpendicularly to the cable and a transmitter for transmitting motion data obtained by this accelerometer set to a remote data processing unit 5. The autonomous device 4 may be inductively powered by the electric current I flowing through the power line 1. The illustrated system must also comprise at least one ambient temperature sensor 6 and one electric current sensor 7, which may be embedded into 4 or using existing remotely installed sensors at substation end and transmitted through dispatching of the system operator, also connected to the remote data processing unit 5. The illustrated system may also comprises one wind speed sensor able to determine the effective wind speed component, which may be embedded into 4 or using existing remotely installed sensors, also connected to the remote data processing unit 5.

[2] Defined on footnote 1

Figure 2:
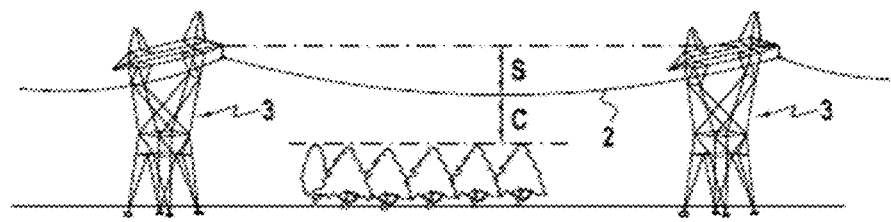
FIG. 2 is a schematic view illustrating a power line with clearance risk evidence, the sag S of the span cannot be too large such that the conductor approaches the obstacle with a distance (or "clearance") C less than a defined minimum value.

Each span 2 has a sag S which will increase with the average temperature $T_c$ of the cable, since thermal dilatation increases the length of the cable between successive pylons 3. Increasing sag of a suspended/anchored cable span always decreases the clearance C of the cable with respect to the ground or any aboveground obstacles, such as trees or buildings, as schematically shown on FIG. 2. It is however often required to maintain at least a critical minimum clearance $C_{min}$ in order to prevent arcing from a suspended/anchored cable span of an overhead high-voltage power line.

It is also required to maintain conductor temperature below a critical maximum value to avoid conductor (and accessories) degradation.

There are various methods for measuring this sag S which are available to the skilled person. For example, in abovementioned U.S. Pat. No. 8,184,015 a method was disclosed for measuring this sag S by analyzing motion sensed by the autonomous device 4.

Sag S may be drawn versus time or current or many other variables.

A generic curve is the sag versus the square of the current, or with an exponent thereof very close to 2. Different curves may be obtained depending on the effective wind speed, ambient temperature and sun radiation, as shown on FIG. 3, FIG. 4 and FIG. 5 respectively.

Figure 3:
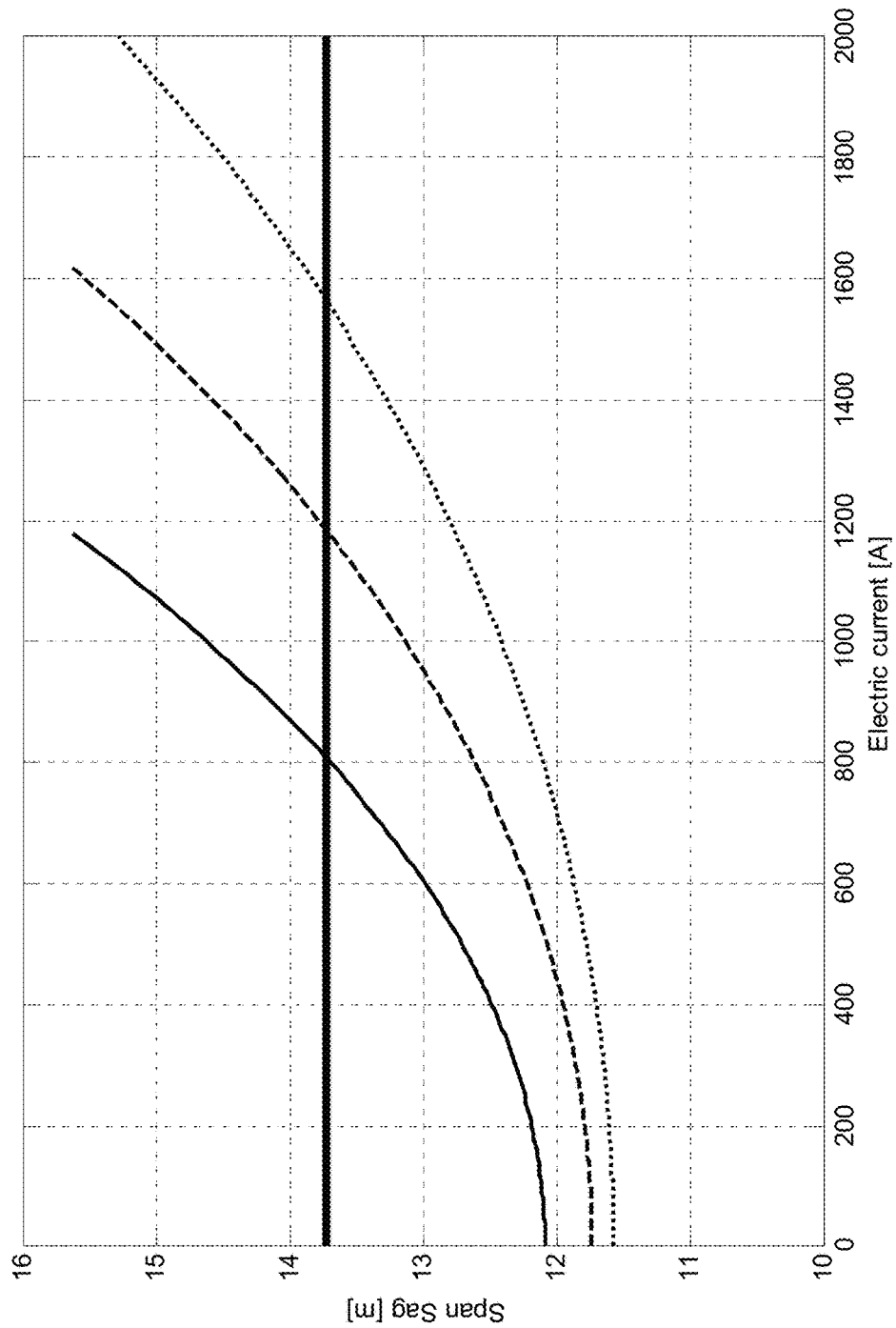
FIG. 3 is a graph illustrating, using IEEE theoretical model, the sag value versus the current flow in the power line. Different curves correspond to different effective wind speeds.

FIG. 3 shows typical conductor sag vs electric current flowing in the line, for different effective wind speeds. IEEE thermal model simulation: $T_a=25°$ C.; $P_{sun}=1000$ W/m$^2$; effective wind speed=0.5 (–), 2 (--), 5 (•••) m/s; thick horizontal line depicts sag value at 75° C.=13.73 m.

Figure 4:
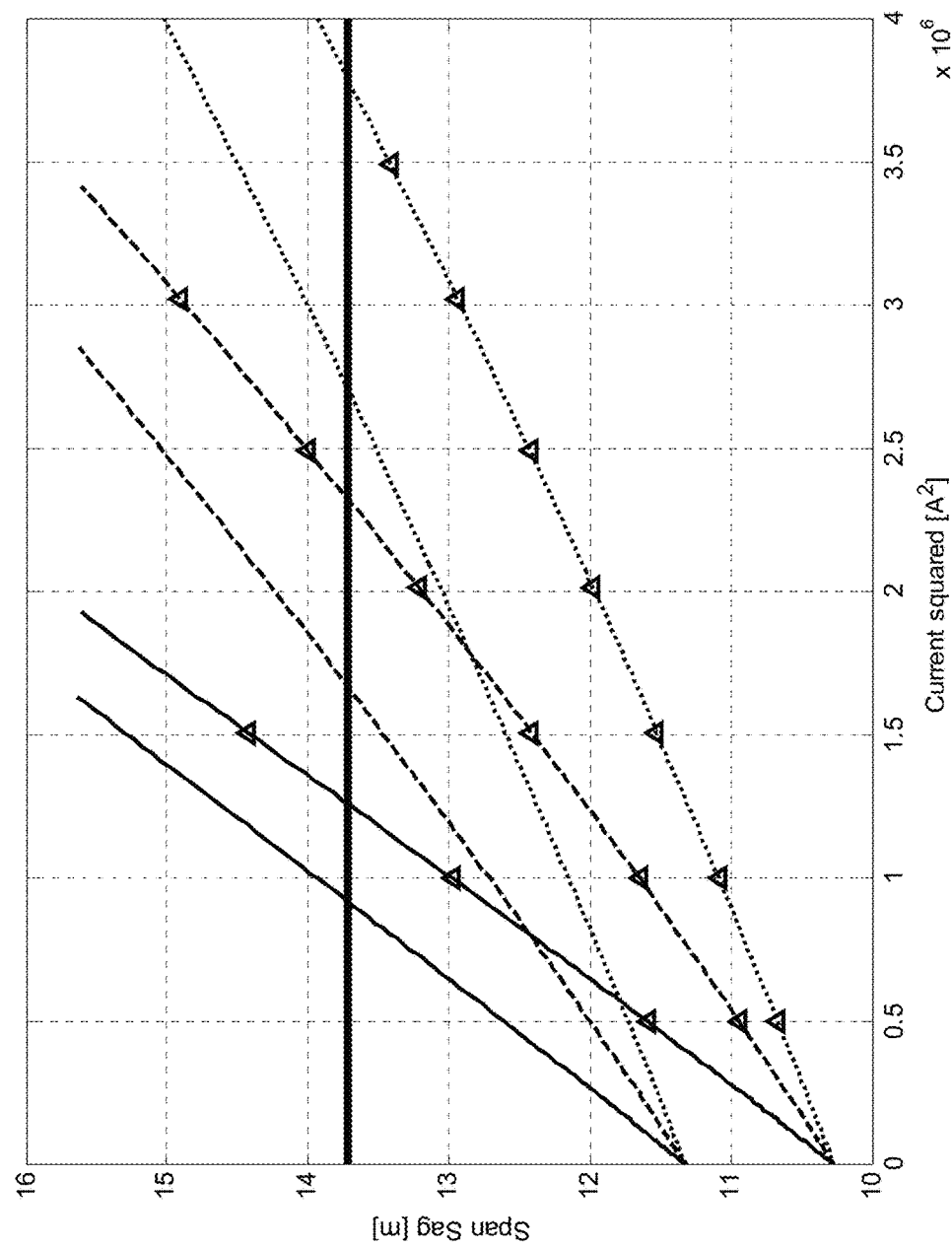
FIG. 4 is a graph illustrating the sag value versus the square of the current flow in the power line for different ambient temperatures and three different effective wind speeds. This is to show the slope correlation between different curves.

FIG. 4 shows sag vs square of the current flow. IEEE Model: $P_{sun}=0$ W/m$^2$. Mixed effects of effective wind speed (0.5 (–), 2 (--), 5 (•••) m/s) and ambient temperature (5° C. (triangle) and 25° C.) parameters; thick horizontal line depicts sag value at 75° C.=13.73 m. At the same effective wind speed the angular coefficient is quasi-identical irrespective of the ambient temperature.

Figure 5:
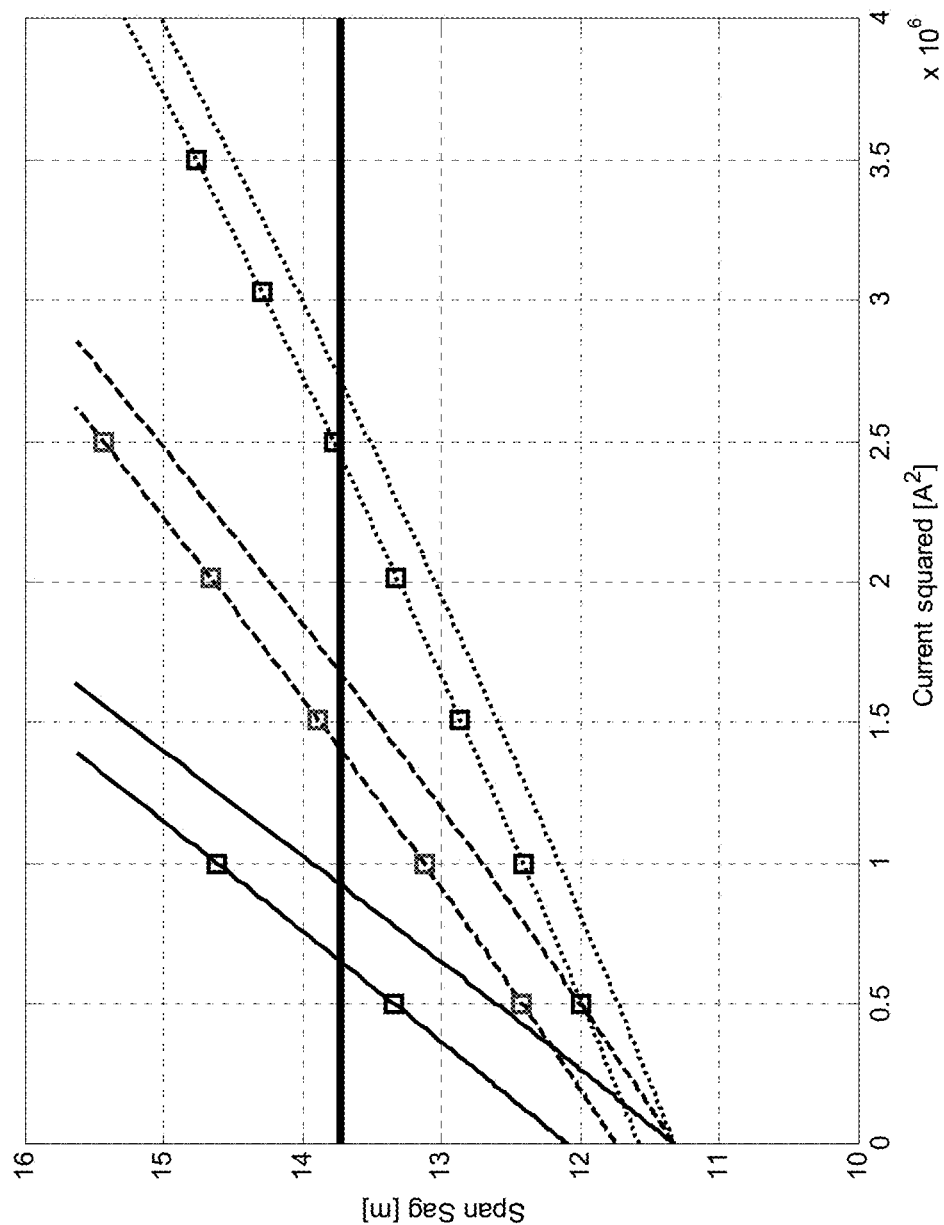
FIG. 5 is a graph illustrating the sag value versus the square of the current flow in the power line for different values of solar radiation and three different effective wind speeds. This is to show the slope correlation between different curves.

FIG. 5 shows sag vs square of the current flow. IEEE Model: $T_a=25°$ C. Mixed effects of effective wind speed (0.5 (–), 2 (--), 5 (•••) m/s) and solar radiation (0 and 1000(□) W/m$^2$) parameters; thick horizontal line depicts sag value at 75° C.=13.73 m. At the same effective wind speed the angular coefficient is quasi-identical irrespective of the solar radiation.

Sun radiation effect as well as ambient temperature effect are basically a vertical shift (for a given effective wind speed), with a typical error less than 5% on ampacity calculated for a maximum sag corresponding to 75° C. if sag vs. I$^2$ is considered, as shown on FIG. 4 and FIG. 5. It means that the rate of change of the curve (which is basically a straight line if abscissa is chosen as the square of the current with a goodness of fit with an R-square over 0.995) is practically not depending on solar radiation nor on ambient temperature.

The apparent linear relationship between the sag and the square of the current is not valid stricto sensu. In fact the resistivity of the conductor is slightly increasing with increased current flow, as this is changing conductor temperature. Radiated heat loss also increases with increasing current flow, as this is changing conductor temperature. Another effect is that geometrical stiffness of sag change with sag itself. Last but not least, expansion of conductor with temperature is not fully linear, especially for HTLS[3] and ACSR[4] conductors and at the "knee-point"[5], but there are workarounds in those cases as detailed further in this document. But these effects are very limited, there are compensations as some effects are slightly increasing the sag rate of change while others are slightly decreasing it and all in one, the global effect is extremely limited in terms of ampacity evaluation.

[3] HTLS=high temperature low sag conductor
[4] ACSR=aluminium conductor steel reinforced
[5] The knee point is related to different dilatation coefficients into some conductors, when they are bi-material (like aluminium-steel in ACSR or aluminium-composite core in HTLS). The sag versus conductor temperature curve is then showing such a knee at a specific conductor temperature, which doesn't evolve significantly over a time span of a few days under normal conditions. Beyond that conductor temperature, the sag rate of change (vs. conductor temperature) is lower.

The method used here is based on actual line behavior instead of being based on models and (sometimes uncertain) data. It is thus valid for any case of multi-span section constitution, including the presence of (very) unequal span length within a line section, (much) unlevelled spans, etc.

Thus, around a given sag (or other variable measured) value, the rate of change of the sag (or other variable measured) w.r.t. the square of the current load flow, depends almost solely on the effective wind speed. Knowing that rate of change of the sag with respect to the current squared allows to calculate the ampacity as described hereinafter.

We first need some months of observations after sensor installation to establish the full cited "rate of change" curve, as different events with different effective wind speeds and different load currents must be observed. A permanent watchdog of these slopes may be settled in order to detect any anomalous change(s) in these data due to abnormal situations (slipping in clamps, broken wires, tower movement, presence of snow, ice, etc.).

An event is defined by a quadruplet:
measured variable by the sensor,
current flow,
effective wind speed,
ambient temperature.

Side variable, if available, is sun radiation. We catch events with a sampling rate of about one minute or a little bit longer depending on the sampling rate used by the sensor, but typically one event ranges in a period less than about 10 minutes.

We will only detail here the case of sag being the "measured variable by the sensor". The adaptation to any other variable of interest may be easily deduced. For example, the inverse of tension in the conductor or the conductor temperature may be used instead of sag if tension is a direct output from the sensor. The corresponding limits for ampacity (minimum tension or maximum conductor temperature) will then be used later on, instead of sag reserve. Nevertheless some of these outputs, like conductor tension, would need extra data and modeling which may not be the case if sag is an output from the sensor. In particular, the sensor described in U.S. Pat. No. 8,184,015 does not need any external data to calculate the sag.

The method consists of three main successive stages:
1) determine the sag-conductor temperature relationship, solely based on observations of concomitant sag and ambient temperature. Use that relationship to update all "quadruplets" into "triplets": ambient temperature and sag can be merged into an "adjusted span sag", which is the sag value at a given constant ambient temperature;
2) determine the rate of change of the adjusted span sag with respect to the current squared (or with an exponent very close to 2). That rate of change is called $\tan(\alpha)$;
3) calculate the ampacity using $\tan(\alpha)$ and sag reserve.

These three stages are further developed below.

Stage 1

Figure 6:
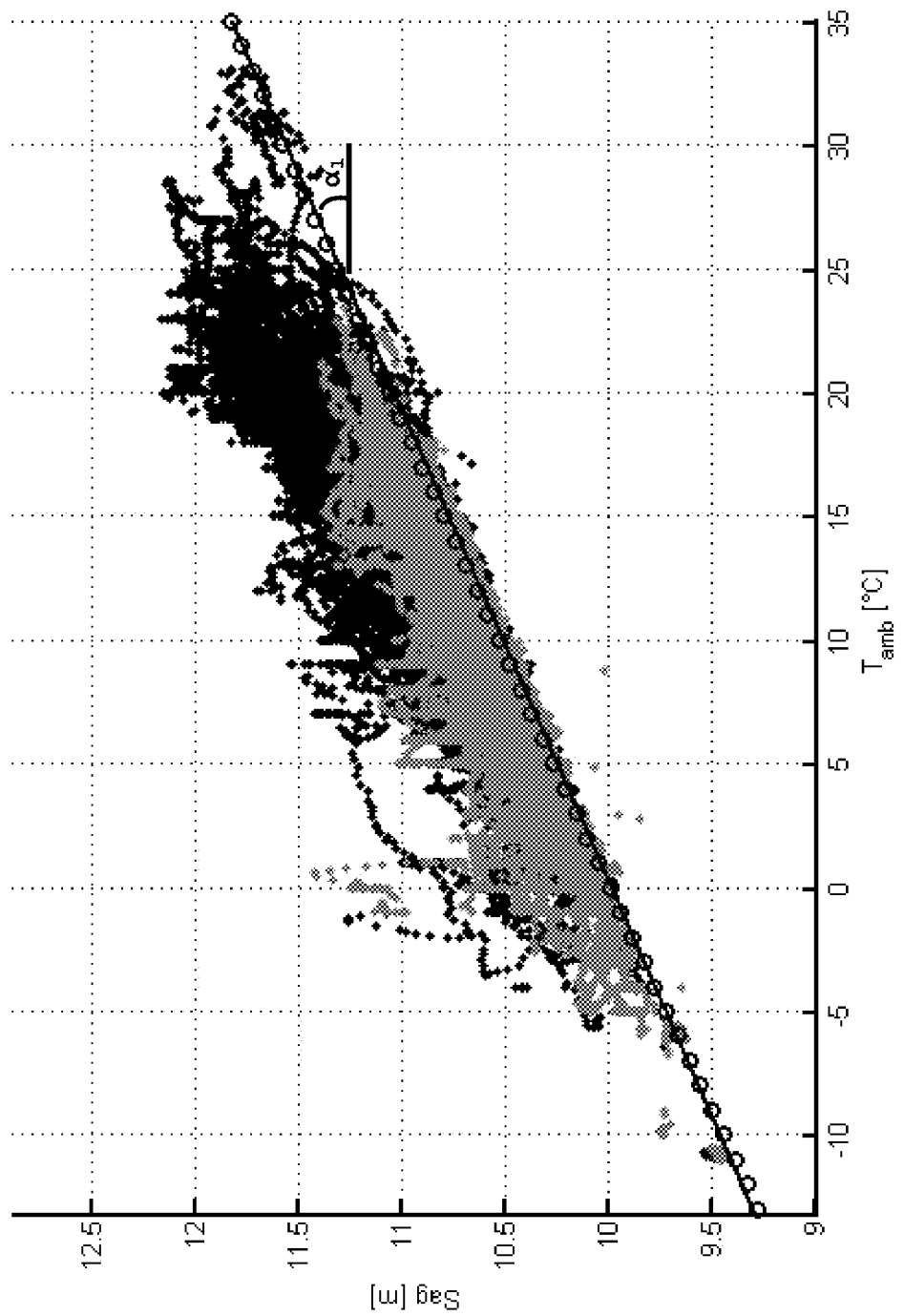
FIG. 6 is a graph illustrating an ensemble of data of measured sag versus ambient temperature in order to get the sag-temperature relationship. This relationship can be obtained by fitting linearly the lower bound of the cloud of points (black dots: mixed day and night observations; greys dots: night observations only)

Data storage is preferably limited to night observations, as the sun radiation effect is then cancelled, but daytime observations could also be used if sun radiation may be quantified reasonably and all dots corrected to cancel sun radiation effect on sag. The relationship between sag and ambient temperature may be obtained without any conductor nor section data, by catching observation points (sag, ambient temperature) as detailed on FIG. 6. In fact measured dots (sag, ambient temperature) are giving a cloud with a cubic (in fact quasi-linear) lower bound curve. Any dots over that line are linked to larger sag occurrences due to solar heating and Joule effect. Any rare dots below that bottom margin are reflecting singular behavior of no interest for these investigations. Hence, the lower bound curve represents the dots for which conductor average temperature equals ambient temperature. FIG. 6 gives such a typical output.

More specifically FIG. 6 shows sag vs ambient temperature during several months (stage 1). The lower-bound cubic fit curve (solid straight line) is also given on FIG. 6 (○).

Linear fit parameters in this case are according to: f=a.x+b, where f is the sag, x the ambient temperature, a=0.053 [m/K] and b=9.98 [m]; $a=\tan(\alpha_1)$ as discussed in the disclosure. That fit is also an image of the in-the-field observed state change equation (like detailed in Kiessling et al, ibid., chapter 14, page 546-553).

Thus a cubic (or quasi linear) fit on the lower bound actually provides the sought sag-conductor temperature relationship (at least valid on ambient temperature range, the only one used in this invention). This, in turn, gives the correction factor needed to adjust the sag value to an identical pre-set reference ambient temperature. The reference temperature may be chosen e.g. as the median of the ambient temperature (for example 10° C.) dataset to minimize the mean absolute error, and hence the approximation error. This allows to shift from the initial quadruplet cited above to a triplet (adjusted sag, current flow, effective wind speed), thus reducing the size of the data base.

The triplets so obtained are preferably grouped by ranges of effective wind speeds. These ranges are chosen using small interval for low effective wind speeds as ampacity is more sensitive for low wind speed ranges, e.g. 0 to 0.5; 0.5 to 1; 1 to 1.5; 1.5 to 2; 2 to 3; 3 to 5; 5 to 7; etc. (Unit: m/s).

Stage 2

Figure 8:
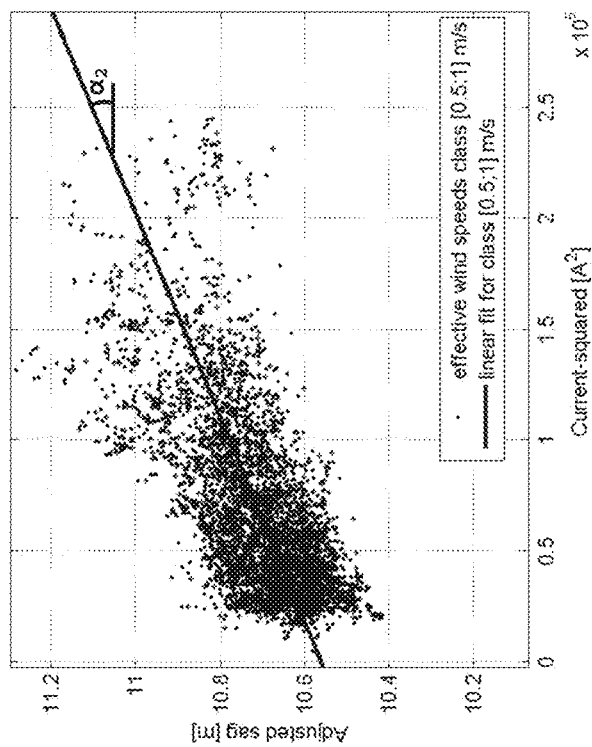
FIGS. 7 and 8 show sag values measured by a sensor in the plane (sag, square of the current flow) during a certain period of time; in this case, sag is given using the above-mentioned U.S. Pat. No. 8,184,015. The different curves correspond to different ranges of effective wind speeds, those wind speeds being evaluated using e.g. PCT patent application PCT/EP2013/055180. All sags have been adjusted to a reference ambient temperature chosen as the median value of the ambient temperature observed over a typical year on site, at 10° C. in this case, using the fit presented in FIG. 6, to determine the correction factor, and drawn during night time so as solar incident radiation remains negligible. The straight lines are the linear fit on the dots at a given range of effective wind speeds.
Figure 7:
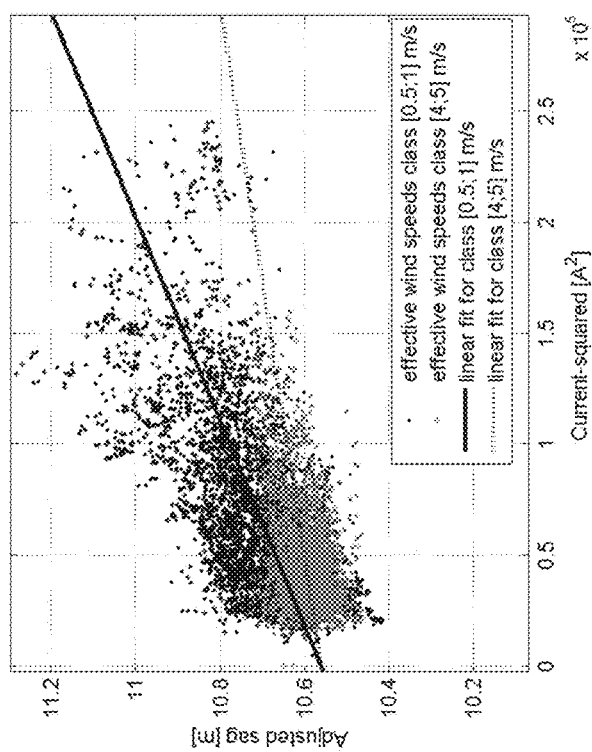

FIGS. 7 and 8 show an example of these data selected and grouped at stage 1. Each dots ensemble corresponding to an effective wind speed range is then fitted by a linear regression. On FIGS. 7 and 8, about 2 years of data are shown.

More specifically FIGS. 7 and 8 adjusted span sag vs. square of the current flow for various classes of effective wind speeds.

The linear fit in this case is: f=a.x+b where f is the adjusted span sag, x the current-squared, and the parameter 'a' found is actually the value of $\tan(\alpha_2)$ [m/A$^2$] sought after for that class of wind speeds.

In FIG. 7, to adjust the span sag, all sag values were shifted to an identical ambient temperature of 10° C., chosen as the median of the ambient temperature dataset. The sag shift is achieved thanks to the cubic (quasi-linear) relationship determined at stage 1, and shown in FIG. 6.

In FIG. 8 are shown details for the lowest range of effective wind speeds (0.5 to 1 m/s).

Most generally a couple of month's records are enough. In particular, satisfactory values for $\tan(\alpha_2)$ were obtained on the tested sample period considering three consecutive months featuring events of current exceeding a third of the seasonal rating for 1.5% of the time on average. Only night time samples were considered.

Figure 9:
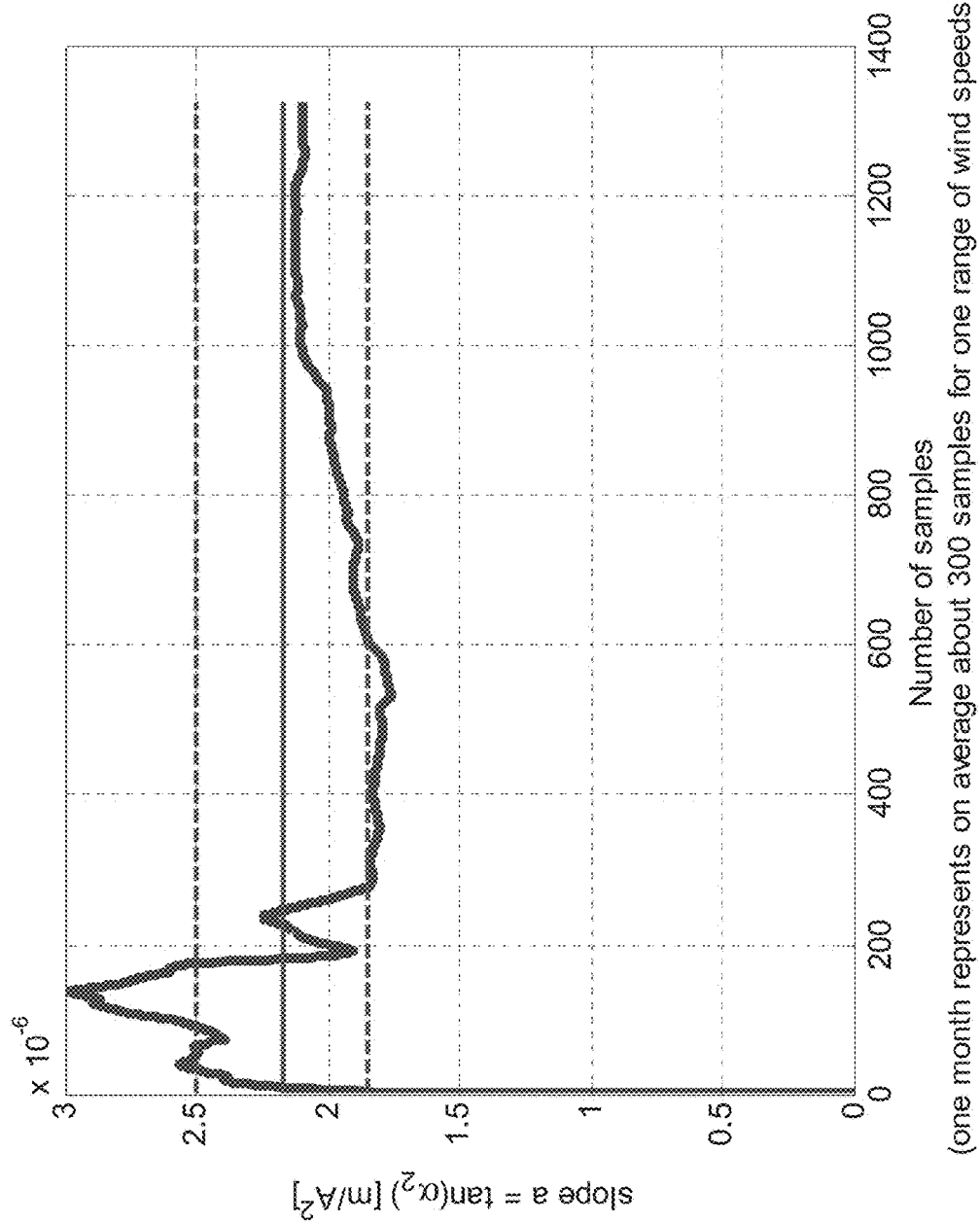
FIG. 9 shows the convergence, vs. the number of successive observations, to the determination of the linear rate of change of the sag value (or the other measured variable) versus the square of the current flow in the power line. In particular this figure is showing angular coefficient convergence of the straight line parameters of the linear fit of the points shown for example on FIGS. 7 and 8, for a given range of effective wind speeds.

FIG. 9 shows the convergence to the final values of $\tan(\alpha_2)$ or the final value for the parameter 'a' of the linear fit described in stage 2 (see FIG. 8) versus the number of samples for wind class (0.5 to 1 m/s). The parameter 'a' is the value of $\tan(\alpha_2)$ sought after, the final value obtained after 30 months is shown (solid horizontal straight line), along with ±15% bounds around the final converged value (dashed straight lines). This example depicts the convergence for three consecutive months for wind class (0.5 to 1 m/s). Three months is also the typical duration needed to achieve satisfactory convergence for all wind classes, given that there is enough occurrences (>1.5%) of high current (>30% I_nominal) during nighttime.

The scattering of data around the linear fit (limited to about +/−10 cm) comprises transients and measurement errors in addition to the class width itself. All these linear fits cross the ordinates axis near the same value which is obviously the unloaded sag at the chosen reference ambient temperature, with no incident radiation from sun.

Figure 10:
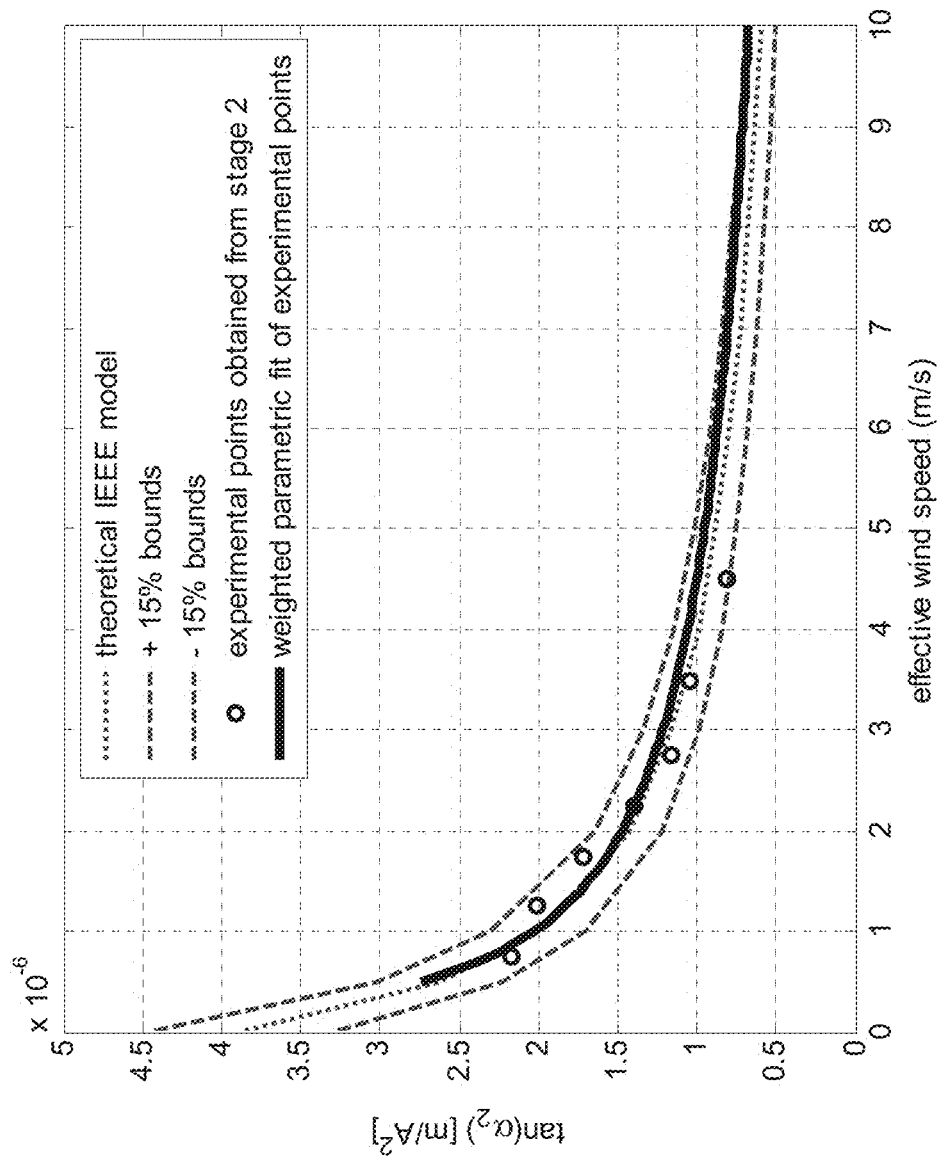
FIG. 10 shows the rate of change, with order of amplitude $10^{-6}$ m/A$^2$, corresponding to angular coefficients of the straight line fits as shown on FIGS. 7 and 8, vs. effective wind speeds. Both the theoretical values and experimental ones deduced from observed sag during a certain amount of time (three months) are shown.

The angular coefficient of the straight line fit is the rate of change of the sag (vs the square of the current flow), for a wind speed value taken as the middle of the effective wind speed class range. The lower the wind speed the higher the rate of change. FIG. 10 shows such a curve fitted on experimental data as obtained in the field with the sensor described in in abovementioned U.S. Pat. No. 8,184,015 and International Publication No. WO 2014/090416. Once that curve has been obtained experimentally for each monitored span, the ampacity can be easily calculated for any monitored span at any moment, on condition that the corresponding triplet of data is available.

Such rate of change versus effective wind speed may be stored in a database until enough dots are available to generate a curve fit of the rate of change versus the effective wind speed (as shown on FIG. 10).

The rate of change, as shown on FIG. 10, may be characterized by the angular coefficient of the straight line ($\tan(\alpha)$). That angular coefficient indeed includes the multi-span effect on mechanical sensitivity of sag evolution, the conductor and line data effect, and the meteorological effects. All in one!

We validate the concept here below by adding some theoretical considerations.

A typical rate of change, given by $\tan(\alpha)$, versus the effective wind speed is drawn on FIG. 10. The theoretical curve, obtained from IEEE model as detailed on IEEE Standard 738-2006—IEEE Standard for Calculating the Current-Temperature of Bare Overhead Conductors, IEEE Power Engineering Society, 2007, is drawn together with a curve fitted on experimental data (by least-square method). This is rare in practice to be able to draw such a curve in direct relation with actual data of the line, but it has been obtained here owing to careful analysis and measurements in the field. The theoretical curve is not needed for this disclosure, as the method described is NOT based on the quantitative aspects of the theoretical curve (some qualitative aspects may be used instead), but on actual measured data. The theoretical curve has been drawn for information and validation purposes of the method described in this disclosure.

The measured $\tan(\alpha)$ curve versus the effective wind speed is then deduced by least square fit. IEEE analysis based on long term empirical observations has in fact fixed the exponent of the wind speed (in the wind cooling effect term) to 0.52 for "low wind speeds" (IEEE Standard 738-2006—IEEE Standard for Calculating the Current-Temperature of Bare Overhead Conductors. IEEE Power Engineering Society. 2006, page 8, equation 3a), and 0.6 at "high wind speeds".

The non-linear fit of the curve may be done using that exponent following equation (1) with c=0.52. The fit may also be evaluated with "c" as an unknown but in a range of value close to 0.52 (range typically close to 0.4 to 0.7):

$$\tan(\alpha) = \frac{a}{b+v^c} \quad (1)$$

where a and b are positive coefficients, "a" typically ranging from $10^{-6}$ to $5 \times 10^{-6}$; "b" typically ranging from 0.10 to about 0.17. Other ranges may easily be found if v is expressed in other units than in m/s. FIG. 9 shows an example of such curve deduced from three successive months observations of "in-the-field" measurement.

FIG. 10 shows $\tan(\alpha_2)$ both in theory and "as observed in-the-field", with its 15% bounds around the theoretical curve. As mentioned above, the in-the-field curve is obtained by applying a weighted parametric fit of the experimental points (0) with equation:

$$\frac{a}{b+v^c}.$$

Those points are the $\tan(\alpha_2)$ values obtained in stage 2 for each class of effective wind speeds. The parameters found here are the following: a=2.349×10$^{-6}$ and b=0.159, and c=0.52 (c has been set beforehand).

Stage 3

Ampacity can then be easily calculated from any real-time measurement: let us consider one measurement featuring a couple (sag, current) for a known effective wind speed. As represented on FIG. 11, P is the point defined by the couple (sag, current-squared) in the plane (sag, square of the current), in the case the square of the current has been chosen in abscissa. We first look up the sag's rate of change ($\tan(\alpha_2)$) for the corresponding effective wind speed from the generic curve formerly established at stage 2 (FIG. 10).

Figure 11:
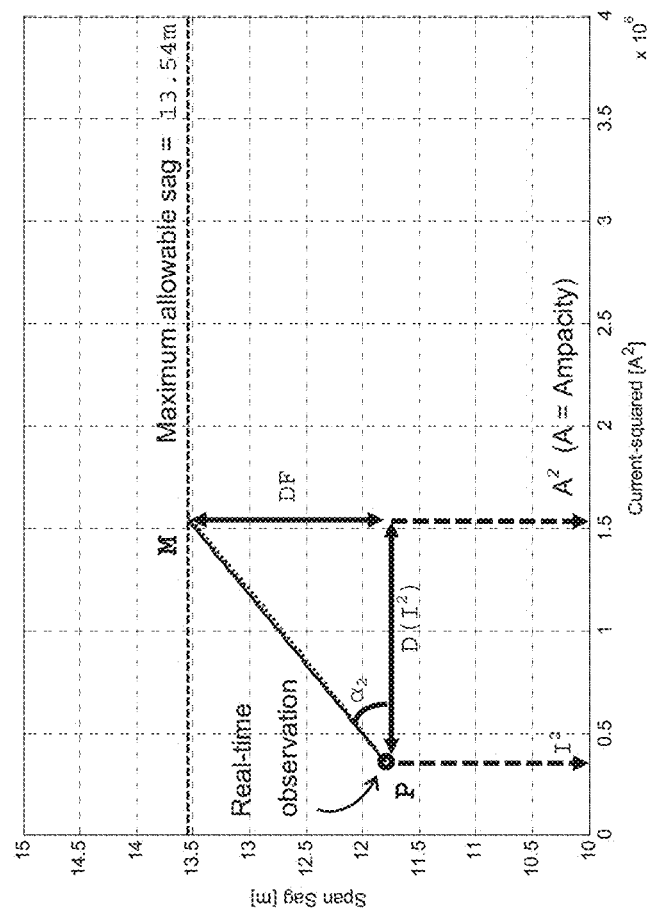
FIG. 11 is a graph illustrating a practical case of ampacity evaluation for a given, but unknown, ambient temperature and sun radiation and for a given and known effective wind speed. An example of application of the disclosure is showing a right-angled triangle with one side equal to the sag reserve (DF) and in front of it the angle $\alpha_2$, illustrating the rate of change of the sag w.r.t. the current-squared for the given effective wind speed. The rating-squared is deduced from the abscissa of the point of intersection between (i) the straight line passing through the measurement point, with a slope equal to the rate of change of the sag at the known effective wind speed, and (ii) the maximum allowable sag.

A right-angled triangle can then be drawn as shown in FIG. 11. Hypotenuse is defined by the straight line passing through P with slope $\tan(\alpha_2)$ which intersects the maximum allowable sag at point M. The abscissa of M corresponds to the ampacity-squared ($A^2$) for this measurement. The ampacity is simply obtained by calculating the square root of that abscissa (formula 2 below).

In more detail FIG. 11 is an illustration of a practical case of ampacity evaluation based on maximum allowable sag (or, in an equivalent way, minimum allowable clearance) for a given, but unknown, ambient temperature and sun radiation and for a given and known effective wind speed (here taken at 2 m/s). This is an example of application of the disclosure showing a right-angled triangle with one side equal to the sag reserve (DF) and opposed to it the angle $\alpha_2$, illustrating the rate of change of the sag w.r.t. the current-squared for the given effective wind speed. The ampacity-squared is deduced from the abscissa of the point of intersection between (i) the straight line (solid straight line) passing through the measurement point (dot P), with a slope equal to the rate of change of the sag $\tan(\alpha_2)$ at the known effective wind speed, and (ii) the maximum allowable sag. One possible theoretical curve is shown as well (dotted curve: $T_a$=20° C., $P_{sun}$=600 W/m$^2$, $v_{eff}$=2 m/s).

This is valid for any sun radiation, any ambient temperature (with no need to know their values) as the rate of change of the sag is almost not depending on these values.

Using actual sag reserve (DF), actual current flow (I) in the line and, for the actual effective wind speed, $\tan(\alpha)$, the actual ampacity of the line is:

$$A = \sqrt{I^2 + \frac{DF}{\tan(\alpha_2)}} \quad (2)$$

of course using a consistent system of units, for example with current and ampacity in amperes, sag and sag reserve in meters. $\tan(\alpha_2)$ may be replaced by $\alpha_2$ as $\alpha$ is very small (order of amplitude $10^{-6}$ m/A$^2$).

Incidentally, the maximum error on ampacity determination can be easily deduced from the formula (2) where variables are considered independent (we neglect the error on the current flow and replace tan($\alpha$) by $\alpha$):

$$\Delta A/A = \tfrac{1}{2}(\Delta\alpha/\alpha + \text{relative error on sag}) \qquad (3)$$

Where the relative error on $\alpha$ term may be expressed versus effective wind speed using formula (1):

$$\frac{\Delta\alpha}{\alpha} = \frac{c}{1+\dfrac{b}{v^c}} \cdot \frac{\Delta v}{v} \qquad (4)$$

As an example, if we may get an error on sag due to the sensor sensitivity at about 2%, then an error of 5% on ampacity would be linked to a 8% error on the rate of change $\alpha$ (using formula 3) or an admissible relative error on wind speed near 1 m/s of about 18% (using formula 4).

Special Case

Consider the case where ampacity is determined first by maximum conductor temperature instead of maximum sag, in particular for High Temperature Low Sag (HTLS) conductors.

Sometimes, as for HTLS conductors, the ampacity is not necessarily coupled with maximum sag anymore (which has nevertheless to be checked as detailed later on) but with maximum allowable conductor temperature, which will need further considerations as detailed below.

The following embodiment is based on available sag values by the sensor. In the case of tension measurement sensor, sag may be deduced from tension and the method detailed below is unchanged. In the case of conductor temperature sensor, the procedure may be simplified as $\beta$ factor (detailed in the procedure below) is obtained straightforward and some steps of the procedure may be skipped.

In this case, two other conductor data are needed: the conductor AC ohmic resistance per unit length $R_0$ at a given reference temperature $T_0$, and k, the temperature coefficient of electrical resistance.

The rate of change $\lambda.\beta$ (defined on FIG. 14) is the initial conductor temperature rate of change versus the square of the current (or an exponent thereof very close to 2). It is dependent on the effective wind speed as shown on FIG. 14. For a given wind speed, that rate of change is almost constant along a significant range of conductor temperature (starting from ambient temperature to about 75° C., depending on conductor type) as typically no knee-point is observed in that curve below that maximum allowable conductor temperature. At higher temperature nevertheless, there are two contradictory effects which are influencing the conductor temperature: the conductor radiation law (being a function of $T^4$ with T in Kelvin) significantly departs from its linear approximation to favor conductor cooling at higher conductor temperature, whereas the change of conductor resistivity (typically increasing with temperature) induces more conductor heating. Both effects can compensate each other on a certain range of conductor temperature but over a given value, resistivity increase is more influencing. Both these effects induce a slightly progressively larger rate of change which may be approximated by the following formula:

Conductor temperature rate of change=$\lambda.\beta + 2.\lambda.\beta^2.k.I^2$ (5)

$\lambda.\beta$ being the initial value of the rate of change in the linear part ($\beta$ is evaluated as detailed later and is dependent of the effective wind speed), where "k" is the temperature coefficient of electrical resistance (typically 0.0036 to 0.004/° C. for aluminum wires), $\lambda$ is a correction factor linked to the reference temperature $T_0$ (very often 20° C.) for AC ohmic conductor resistance (given by formula 7).

In other words, conductor temperature versus the square of the current may be written as follows:

$$T_c - T_{c0} = \lambda.\beta.I^2 + \lambda.\Delta^2.k.(I^2)^2 \qquad (6)$$

$T_{c0}$ being the initial conductor temperature at no electrical load.

$$\lambda = (1+k(T_{c0}-T_0)) \qquad (7)$$

The approximations (5) and (6) are valid until about 150° C. (FIG. 14F). Over that value, we recommend to keep using the same equations as the corresponding evaluation will be always conservative for ampacity determination based on maximum conductor temperature.

Figure 12:
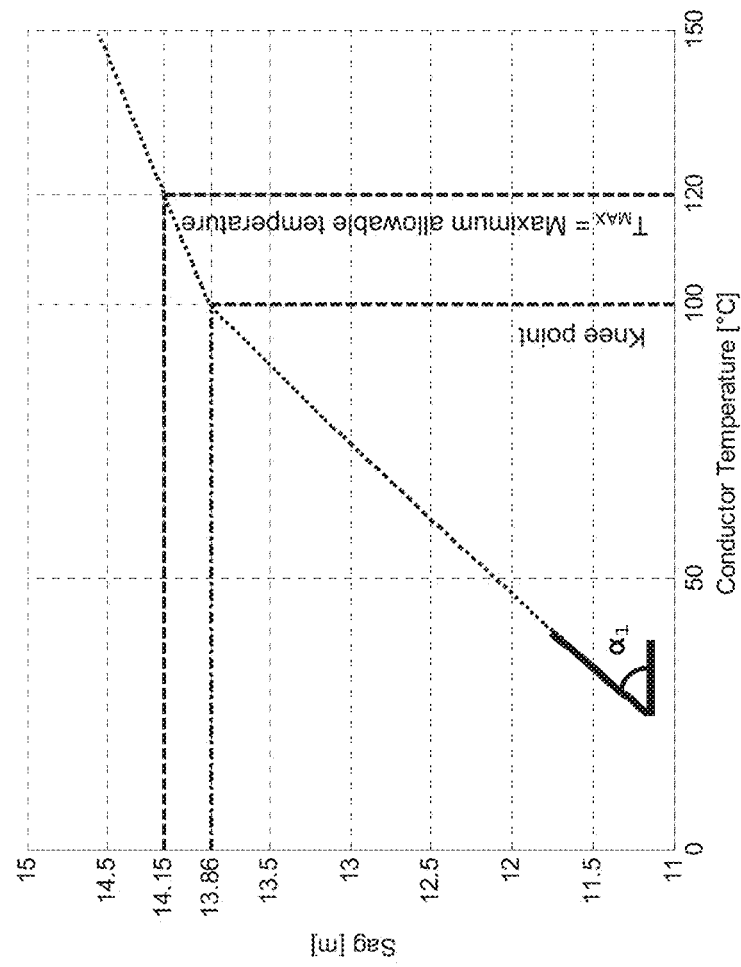
FIGS. 12-14 illustrate the case of HTLS conductor, with its non-linear behavior due to varying coefficient of thermal expansion depending on the conductor temperature, with a change of the curve slope sag-conductor temperature at the so-called knee-point, when aluminum wires are being slightly compressed and either steel or composite core carries all the tension.
Figure 13:
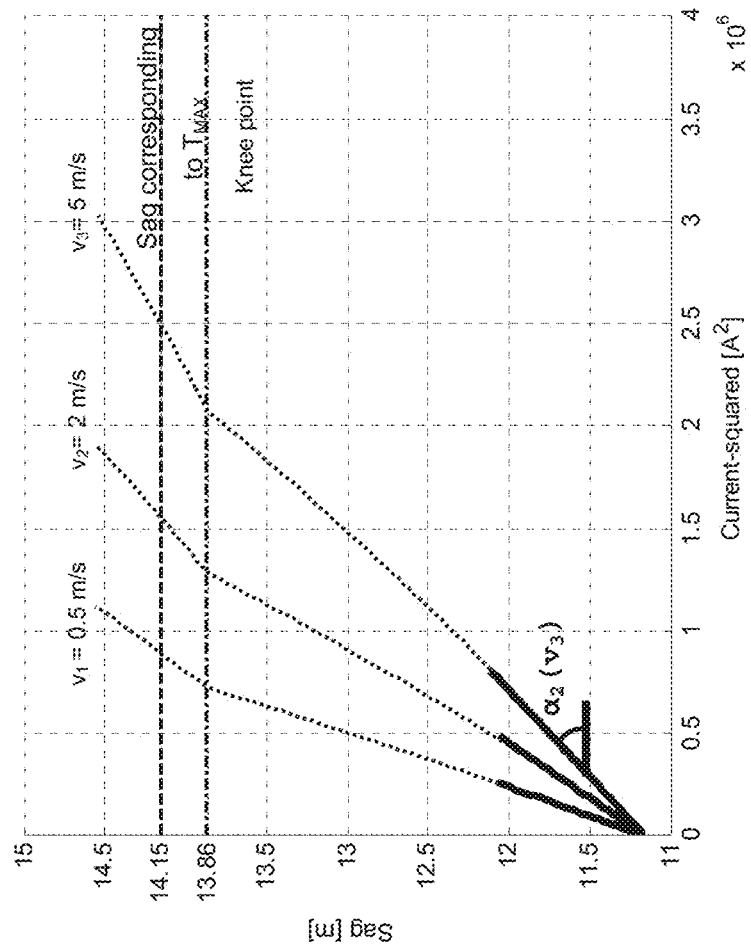
Figure 14:
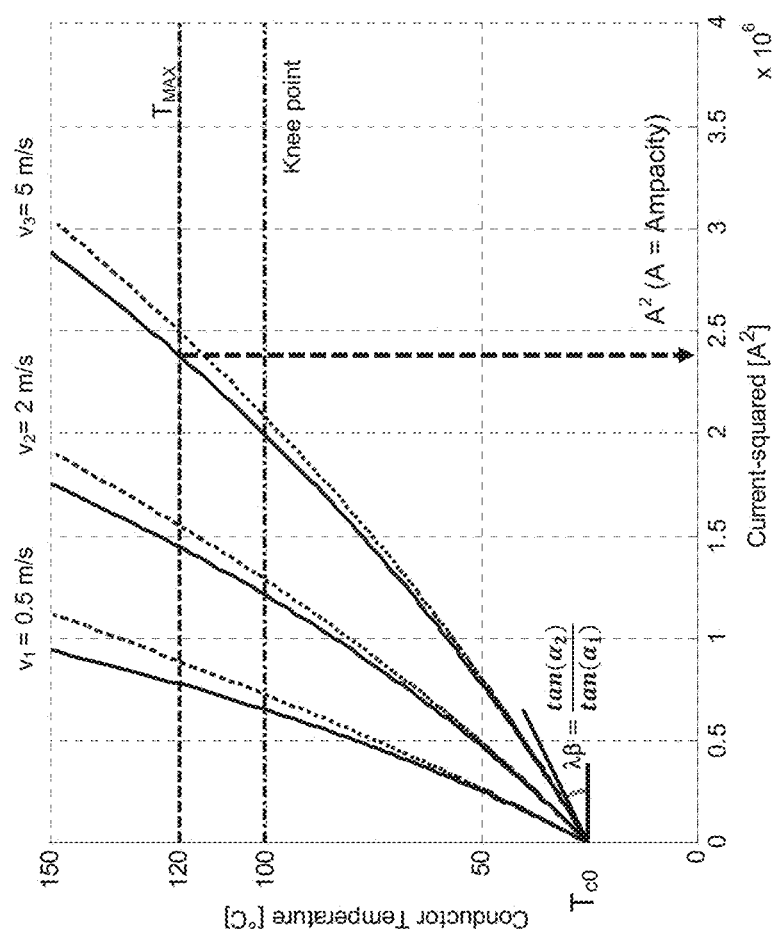

FIGS. 12-14 illustrate the special case for HTLS or ACSR conductors, featuring a knee-point behaviour for the sag. The knee-point has been set at 100° C. in this example. An example of ampacity evaluation (A) based on maximum allowable conductor temperature ($T_{max}$) is shown, A also being given by equation (9) below in this disclosure.

FIG. 12 is the sag versus conductor temperature with a curve slope below the knee-point equal to $\alpha_1$. It is obtained in a similar way as on FIG. 6. In this case tan($\alpha_1$)=0.039 [m/K].

FIG. 13 is the sag of the conductor span versus the square of the current flow, depending on the effective wind speed v, with a curve slope below the knee-point equal to tan($\alpha_2$)≈$\alpha_2$ which is the same $\alpha_2$ as the one shown on FIG. 10.

FIG. 14 is the conductor temperature versus the square of the current flow with a slope parameter $\lambda\beta$, depending on the effective wind speed v, with $\lambda\beta$=tan($\alpha_2$)/tan($\alpha_1$).

Dotted curves are IEEE-computed. Solid curves are an approximation using $\alpha_1$ and $\alpha_2$. $T_{c0}$ is computed by using formula (6) of the disclosure. ACCR conductor (Hawk 477) is with the same line parameters as in the base case. Knee point is defined at 100° C. Maximum allowed conductor temperature is set at 120° C.; $T_a$=25° C.; $P_{sun}$=0 W/m²; effective wind speeds equal 0.5, 2, 5 m/s respectively.

Typical conductor temperature increases (over initial value) are shown on FIG. 14 by different ranges of effective wind speeds. The equation 6 is also shown on the same figure and is drawn up to 150° C. On the same figure the IEEE model has also been used for comparison and validation of the proposed method.

If a conductor replica is used, $T_{c0}$ is known without any other needs. If not, following procedure may be applied to catch it.

During night time, the initial conductor temperature at no load ($T_{c0}$) is the ambient temperature $T_a$ (if we neglect albedo). During sunny days, a correction must be applied depending on sun radiation and wind speed. If no information is available about actual sun radiation, theoretical value may be used as it will give a conservative value for ampacity based on maximum conductor temperature. The corresponding initial conductor temperature at no load is thus calculated as follows:

$$T_{c0} = T_a + (\beta.\alpha_s.S_{un}.d)/R_0 \qquad (8)$$

where "$S_{un}$", given in W/m², is the sun radiation at the location. If unknown, theoretical maximum value can be calculated using formula detailed in IEEE Standard 738-2006 for calculating the current-temperature of bare overhead conductors, published in 2006, page 9, formulae 8 and 9. If albedo needs to be included, it has to be inserted here; $T_a$ is the ambient temperature (° C.); d is the conductor external diameter (m); $\alpha_s$ is the conductor absorptivity (take 0.9 as recommended by CIGRE Technical Brochure No. 299, page 22—"Guide for selection of weather parameters for bare overhead conductor ratings", published in 2006); $R_0$ is the AC conductor ohmic resistance per unit length (Ω/m) at the frequency of the network (50 or 60 Hz). It is given at a reference temperature $T_0$ (most generally $T_0=20°$ C.) and β is the main part of the initial conductor temperature rate of change detailed below. It depends on the effective wind speed.

Conductor temperature rate of change w.r.t. the square of the current (formula 5) is not affected by the knee-point. In fact it is guided by the heating up of the aluminum layer. The initial rate of change λ.β shown on FIG. 14, is the ratio between two other rates of change, λ.β=tan($\alpha_2$)/tan($\alpha_1$), which are known from this disclosure:

(1) tan($\alpha_1$) is the rate of change of the sag versus the conductor temperature (linear fit shown on FIG. 6), before reaching the knee-point, if any (FIG. 12);

(2) tan($\alpha_2$) is the rate of change of the sag w.r.t. the square of the current flow (FIGS. 7 and 9). This last value is also being chosen before reaching the knee-point, if any. (FIG. 13).

Using formula (1) for tan($\alpha_2$), λ can be expressed in an analytical way, only depending on effective wind speed, for this procedure.

The starting point of the conductor temperature curve, at zero current flow, is designated $T_{c0}$, close to ambient but not identical during sunny days, as detailed here above by formula (8).

Computation of Ampacity Based on Maximum Conductor Temperature

Knowing the maximum available conductor temperature, $T_{max}$, fixed by conductor manufacturer with an acceptable margin, or fixed by the law, or by power line owner, the ampacity linked to that value is then easily obtained, as shown on FIG. 14, solving equation (6) with the current flow "I" as the unknown and $T_c=T_{max}$. It depends on the effective wind speed as β depends on it. Thus:

$$\text{Ampacity} = \sqrt{\frac{-1 + \sqrt{1 + \frac{4k}{\lambda}(T_{max} - T_{c0})}}{2\beta k}} \quad (9)$$

with k in ° C.$^{-1}$, β in ° C./A$^2$, temperatures in ° C., ampacity in amperes.

A redundant security information may be obtained in the case of patent U.S. Pat. No. 8,184,015, with an independent sag alert.

(End of Special Case).

Figure 15:
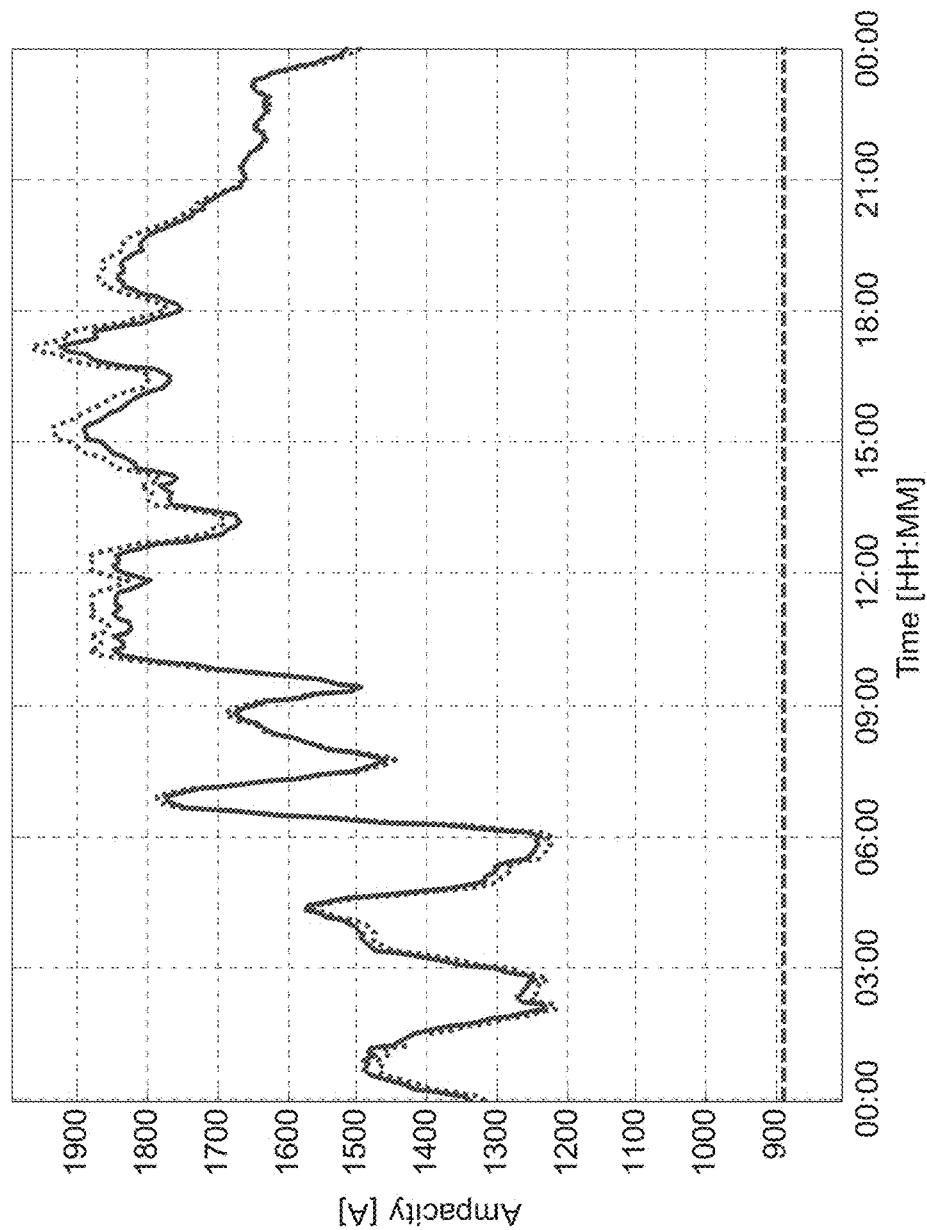
FIG. 15 is a graph illustrating the time evolution of the maximum allowable current rating, calculated according to a method of the present invention and compared with a conventional seasonal rating.
Figure 16:
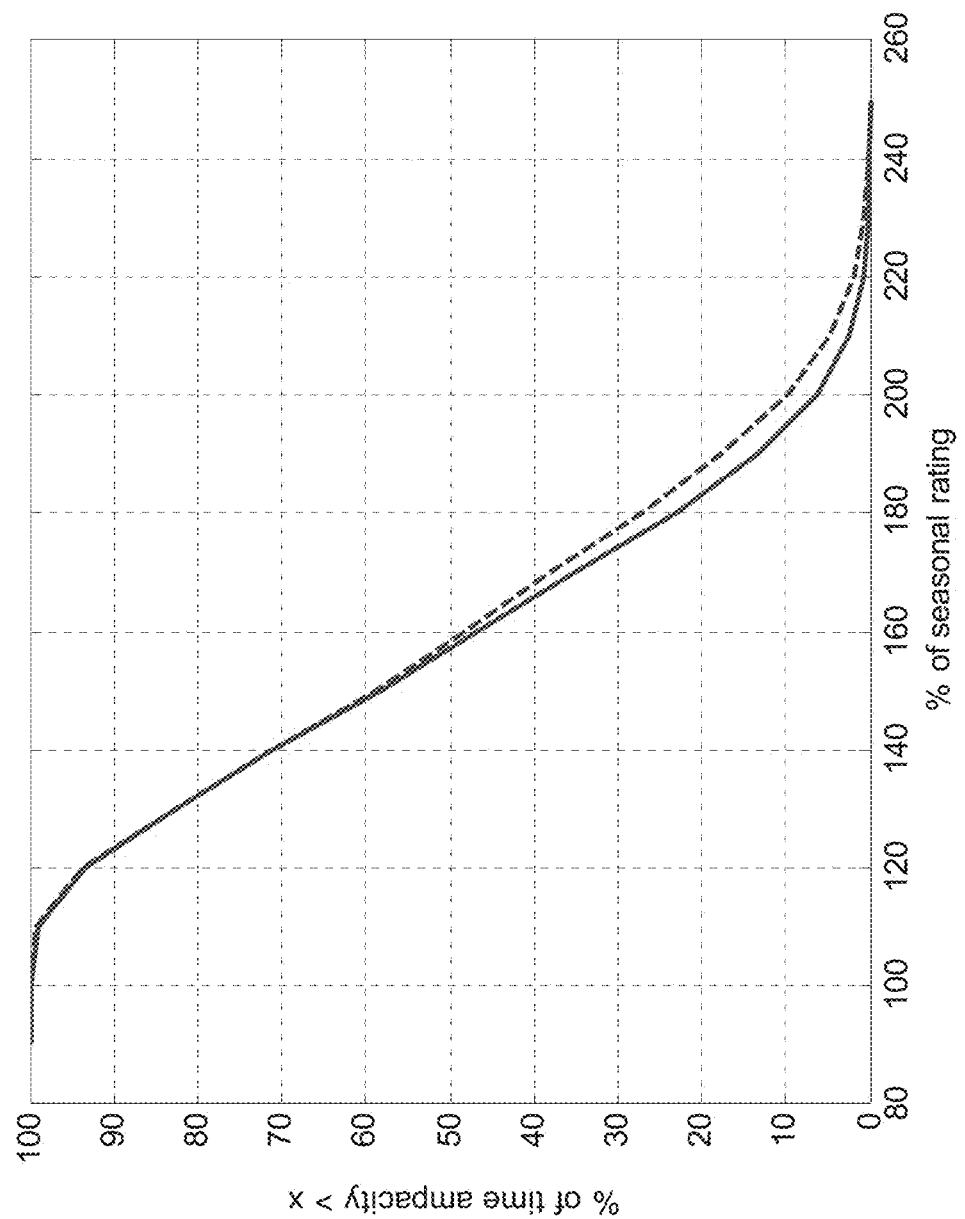
FIG. 16 is a graph showing cumulative histogram of maximum allowable current rating for more than one year, calculated according to a method of the present disclosure (solid curve), as compared with IEEE method.

FIG. 15 represents time evolution of ampacity compared with the actual current I over one full day by both this disclosure and IEEE theoretical model. FIG. 16 represents cumulative distribution of ampacity over static or seasonal rating of one year using either this disclosure and IEEE theoretical model. Both figures illustrate the evolution of the maximum allowable current rating $I_{max}$ or ampacity calculated using this disclosure through the same suspended/anchored cable span 2 over the same period. As shown in these figures, this method offers a dynamic current rating that is significantly higher than the static rating over the entire 24-hour period. This can, for instance, help the integration of highly variable power sources in the power grid, and in particular of renewable power sources such as wind power.

In particular FIG. 15 shows time evolution of the maximum allowable current rating, calculated according to a method of the present disclosure (solid curve), compared with a conventional seasonal rating (dashed straight line), and with IEEE method using sag values, effective wind speeds, measured ambient temperatures and deduced sun irradiance (dotted curve).

In particular FIG. 16 shows cumulative histogram of maximum allowable current rating for more than one year, calculated according to a method of the present disclosure (solid curve), compared with IEEE method using sag values, effective wind speeds, measured ambient temperatures and deduced sun irradiance (dashed curve). In general, the method of the present disclosure provides more conservative maximum allowable current ratings than the IEEE method.

The maximum allowable current rating $I_{max}$ may be calculated for at least each critical suspended/anchored cable span 2 of the power line 1. The lowest value of that set of maximum allowable current ratings $I_{max}$ for these individual suspended/anchored cable spans 2, points out the most constrained link in the power line 1. That value is therefore the maximum allowable current rating for the entire power line 1, which will be used to limit the electric current supplied through the power line 1.

The long term forecasted ampacity may be calculated with the same method, once the rate of change versus the effective wind speed has been obtained for the power line. In that case, forecasted effective speed is needed over the time period needed. The way to produce such forecasted effective wind speed and other needed meteorological data is not included in this disclosure.

The remote data processing unit 5 may be a conventional programmable computer running a computer program implementing these methods.

This computer program may be in the form of a set of instructions stored in a memory carrier. In the present context, "memory carrier" should be understood as meaning any physical medium capable of containing data readable by a reading device for at least a certain period of time. Examples of such memory carriers are magnetic tapes and discs, optical discs (read-only as well as recordable or re-writable), logical circuit memories, such as read-only memory chips, random-access memory chips and flash memory chips, and even more exotic data storage media, such as chemical, biochemical or mechanical memories.

Although in the illustrated embodiment the data processing unit 5 is remote from the autonomous device 4, it could also be completely or partially integrated into one such autonomous device 4, so that at least some of the computing steps of these methods are carried out within the autonomous device 4 itself.

Those skilled in the art will recognize that the present invention may be manifested in a variety of forms other than the specific embodiments described and contemplated herein. Accordingly, departure in form and detail may be made without departing from the scope of the present invention as described in the appended claims.

The invention claimed is:

1. A method for measuring the power line thermal rating or maximum allowable current rating of an overhead power line with respect to a suspended/anchored cable span, using an autonomous device clamped thereon and remotely connected to a data processing unit, comprising an accelerometer set, and using an electric current sensor, an ambient temperature sensor and a wind speed sensor, said method comprising at least the following steps of:

monitoring with the accelerometer a motion of at least one point P of said suspended/anchored cable span in at least two axes perpendicular to the cable over a time interval, the accelerometer signal being directly related to an actual sag of the suspended/anchored cable span;

monitoring with the current sensor an actual line current I, in ampere, over said time interval;

measuring or determining with the wind speed sensor the effective wind speed of said suspended/anchored cable span over said time interval, said effective wind speed being the middle value of a wind class range; and by using the data processing unit:
determining the relationship between said sag values and a measured cable temperature and adjusting said sag values for temperature in order to get a temperature independent actual sag;

determining said sag of said suspended/anchored cable, as a variable of actual line current;

determining a sag reserve DF, in meters, for thermal rating, which is the distance between the actual sag and a maximum allowable sag;

determining the rate of change, tan (a), in meter/ampere$^2$, of said actual sag versus the square of the line current for the effective wind speed, said rate of change being the slop or angular coefficient of a linear fit to the points (x,y), wherein x equals current-squared and y equals said actual sag; and determining the power line thermal rating of the overhead power line, or ampacity, linked to a corresponding safety clearance, at measured or determined effective wind speed, by adding the square of actual current I to the ratio of the sag reserve DF by the sag rate of change, tan (a), at the effective wind speed, and taking the square root of that addition, i.e.

$$\text{Ampacity} = \sqrt{I^2 + \frac{DF}{\tan(\alpha)}},$$

wherein ampacity is in amperes.

2. The method according to claim 1, wherein the variable sag is replaced by a variable selected from the group consisting of conductor temperature, tension, position and any other indirect variable representative of the sag, and wherein the sag reserve variable is optionally replaced by the temperature margin between an actual temperature and a predetermined maximum allowable temperature for power line thermal rating, the sag rate of change being then replaced by the rate of change of conductor temperature.

3. The method according to claim 1, wherein, in said step of determining the sag rate of change, the latter is determined using the slope of the linear fit of the actual sag versus the square of the current, or an exponent thereof very close to 2, on available data for measured sag, load current, ambient temperature and for a given effective wind speed or range thereof.

4. The method according to claim 3, wherein the determination of the sag rate of change for a given effective wind speed or range thereof is performed on different time scales, typically around three months.

5. The method according to claim 1, wherein, preferably in case of HTLS conductor, when ampacity is primarily limited by a maximum temperature instead of a maximum sag or minimum clearance, the method comprises the following further steps:

determining $\tan(\alpha_2)$, in meter/ampere$^2$, similarly as in claim 1, which is the sag rate of change versus the square of the line current, this value of the sag rate of change being chosen before reaching a knee-point of the curve, if any;

determining $\tan(\alpha_1)$, in meter/° C., which is the sag rate of change versus the conductor temperature according to a linear fit, before reaching a knee-point, if any;

determining $\lambda.\beta = \tan(\alpha_2)/\tan(\alpha_1)$ with $\lambda = (1 + k(T_{c0} - T_0))$, wherein k is the linear temperature coefficient of conductor ohmic resistance, in ° C.$^{-1}$;

$T_{c0}$ is the conductor temperature extrapolated at no load in the same meteorological conditions, in ° C.;

$T_0$ is the reference temperature for the ohmic resistance of the conductor, in ° C.;

knowing the maximum available conductor temperature $T_{max}$, calculating the ampacity, in amperes, linked to that value by the formula:

$$\text{Ampacity} = \sqrt{\frac{-1 + \sqrt{1 + \frac{4k}{\lambda}(T_{max} - T_{c0})}}{2\beta k}}$$

with $\beta$ in ° C./ampere$^2$.

6. The method according to claim 5, wherein the maximum available conductor temperature $T_{max}$ is fixed by a conductor manufacturer with an acceptable margin, or fixed by legal provisions, or fixed by a power line owner.

7. The method for supplying electric power over a power line comprising a suspended/anchored span of electrically conductive cable, comprising the steps of:

determining a maximum allowable current rating for said suspended/anchored span of electrically conductive cable according to the method according to claim 1; and limiting a current passing through said power line at or below said maximum allowable current rating.

8. A non-transitory computer readable medium containing computer instructions stored therein for causing a computer processor to perform the steps of the method according to claim 1 when executed by the computer processor, when said computer processor is connected to a sensor set for sensing the motion of at least one point of said suspended/anchored cable span, the line current and the conductor or ambient temperature over a time interval.

* * * * *